United States Patent [19]
Martindale

[11] Patent Number: 5,465,765
[45] Date of Patent: Nov. 14, 1995

US005465765A

[54] VACUUM APPARATUS FOR DEVELOPING FINGERPRINTS

[76] Inventor: Jack E. Martindale, 407 County Line Rd., Royce City, Tex. 75089

[21] Appl. No.: 228,099

[22] Filed: Apr. 15, 1994

[51] Int. Cl.$^6$ .................................................... A61B 5/117
[52] U.S. Cl. ................. 141/65; 141/51; 141/63; 141/70; 141/89; 118/31.5
[58] Field of Search ................... 141/8, 11, 51, 141/63, 65, 66, 69, 70, 89, 98; 118/31.5, 50; 427/1

[56] References Cited

U.S. PATENT DOCUMENTS

| | | | |
|---|---|---|---|
| 1,642,577 | 9/1927 | Carson | 141/51 X |
| 1,770,380 | 7/1930 | Young | 141/66 |
| 2,415,409 | 2/1947 | Birkland | 141/8 |
| 2,862,307 | 12/1958 | Bloomer et al. | 141/51 X |
| 4,172,477 | 10/1979 | Reich | 141/8 |
| 4,297,383 | 10/1981 | Bourdon | 427/1 |
| 4,836,233 | 6/1989 | Milgate, III | 118/50 X |
| 5,217,053 | 6/1993 | Foster et al. | 141/98 |
| 5,266,112 | 11/1993 | Crosbie | 118/31.5 |
| 5,275,215 | 1/1994 | Derby | 141/65 X |

OTHER PUBLICATIONS

Payton Scientific Inc. *CYVAC Preliminary Instruction Manual*, Feb. 1993.

*Primary Examiner*—J. Casimer Jacyna
*Attorney, Agent, or Firm*—Richards, Medlock & Andrews

[57] ABSTRACT

A vacuum chamber is provided for the development of latent fingerprints, having a first and second end, and end plates sealing the first end, a removable end plate for sealing the second end to form a vacuum chamber by assembly of the wall end plates. In addition, the chamber wall and end plates define three passageways, a vacuum gauge passageway, an inlet passageway and an outlet passageway. The outlet passageway is connected to a conduit which is connected to the inlet of a vacuum pump. The outlet of the vacuum pump is connected to a conduit connected to a valve assembly, and the valve assembly is connected to a recycle conduit, and the recycle conduit is connected to the inlet passageway. The valve assembly has a first position whereby gases within the chamber are vented to the atmosphere and recycle is prevented, and a second position in which recycle of gases remaining in the chamber is permitted while venting to the atmosphere is prevented.

13 Claims, 3 Drawing Sheets

VACUUM APPARATUS FOR DEVELOPING FINGERPRINTS

TECHNICAL FIELD OF THE INVENTION

The present invention relates to forensic equipment, and in particular, a vacuum chamber for use in developing fingerprint evidence.

BACKGROUND OF THE INVENTION

It is well known in the field of law enforcement to use fingerprints for identification of suspects. Early on, fingerprints were located by dusting, a process in which a commercially prepared fingerprint powder consisting mainly of carbon black and fluorescent powder carried on plant spores and adhered to the moisture left by a print on a surface. After the prints were dusted, the prints were lifted using a transparent tape, such as Scotch® transparent tape. The system suffered several drawbacks, including that prints were frequently overlooked, that the print could easily be destroyed by improper handling and that the lifted print was not easily usable in later identification procedures.

Subsequently, there developed the process of developing prints by placing a piece of evidence in a container, such as an aquarium, with a small amount of cyanoacrylate ester, which was heated so that it would fume. A useful form of cyanoacrylate ester is commonly available as the principal ingredient in Super Glue®. As the ester was boiled, the chamber filled with fumes, and the fumes reacted with moisture retained in the print to create a polymer. This polymer made a hard representation of the print. The problems with this procedure are that the cyanoacrylate ester had to be heated, producing a dense, white smoke. The large quantity of fumes are irritating to the eyes and respiratory system of the operator when opening the chamber. Furthermore, the possibility existed that an operator wearing contact lenses could have the contact lenses adhere to the eyes if exposed to the dense fumes. These fumes are reactive with moisture and, thus, excess moisture on the piece of evidence could react with the fumes and obliterate the print.

More recently there has been an improvement in the cyanoacrylate ester method whereby evidence is placed in a vacuum chamber, the pressure is reduced in the vacuum chamber, and with a slight amount of heat, the glue is boiled and the print will develop. Such a chamber is sold by Payton Scientific, Inc. under the trade name Cyvac. The Cyvac chamber utilizes two pumps and a series of values. The Cyvac chamber has the disadvantages of complex construction, poor circulation of fumes within the chamber, and the possibility of operator error. In addition, the Cyvac device is quite expensive.

Thus, there has been a need in the art to provide a vacuum chamber of simple construction, with minimum parts, with circulation which assures good print development, and a mechanism to prevent destruction of prints by operator error and at the same time be economical.

SUMMARY OF THE INVENTION

In one aspect the present invention relates to a vacuum chamber for development of fingerprints. The chamber is formed by a wall defining a volume, having first and second ends, first and second end plates which can be positioned at the first and second end of said wall to form the vacuum chamber. The thus formed vacuum chamber further defines three passageways, a vacuum gauge passageway, an outlet passageway and an inlet passageway. In the preferred embodiment these passageways are located within the wall. The outlet passageway is connected to the inlet of a vacuum pump. The outlet of the vacuum pump is connected to a vacuum outlet conduit, which is in turn connected to a valve assembly. The valve assembly is connected to a recycle conduit, which is connected to the inlet of said inlet passageway of the chamber. The valve assembly has two position, the first position being one where gases are vented to the atmosphere, which are pumped from the chamber and recycle of gases to the chamber is prevented. In the second position the valve assembly allows recycle of gases within the chamber while preventing exhaust of gases to the atmosphere. The valve assembly may be two separate valves, or a single valve.

In the preferred embodiment the device is automated with a vacuum switch attached to the vacuum passageway and the valve assembly is actuated by a solenoid. When a sample is placed in the chamber and the end plates are secured in place, the vacuum pump is started and the valves are set in the exhaust position. When the vacuum within the chamber reaches a predetermined level, the switch trips the solenoid, closing the exhaust valve and activating the recycle valve. After the gases within the chamber have been recycled for a predetermined time to achieve development of any latent fingerprints on the specimen inserted, the vacuum pump is cut off, causing the solenoids to open the vent valve.

BRIEF DESCRIPTION OF THE DRAWINGS

The invention will be more fully appreciated with reference to the detailed description in conjunction with the drawings which are.

DETAILED DESCRIPTION

Figure 1:
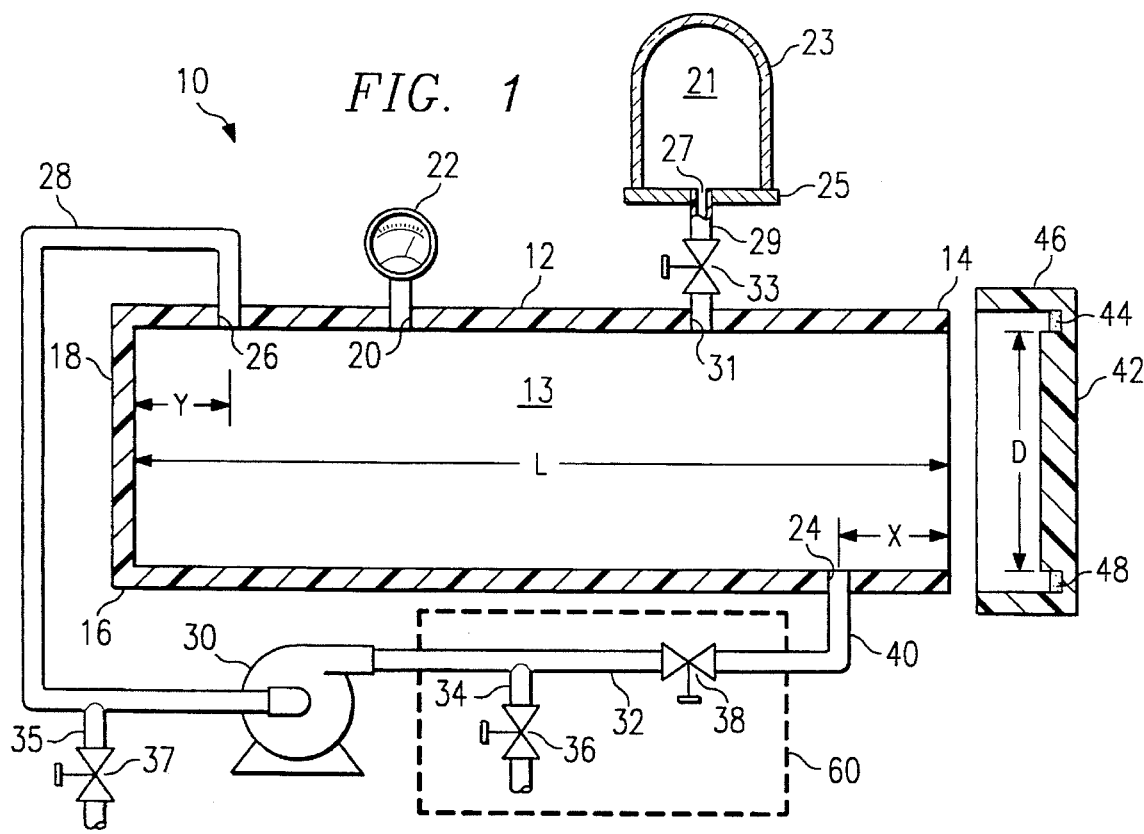
FIG. 1 is a cross sectional view of one embodiment of the present invention.

FIG. 1 shows a cross sectional view of one embodiment of the fingerprint developing chamber of the present invention generally indicated as 10, which comprises a wall 12 defining a chamber 13 and a number of passageways. Wall 12 has a first end 14 and a second end 16. Preferably wall 12 is cylindrical in configuration and at second end 16 is end plate 18 to form an air tight seal at the second end of said chamber. Second end 18 may be formed integrally as part of wall 12 or may be a separate piece which is affixed to wall 12. Alternatively, end plate 18 may be a removable end piece. Wall 12 also defines gauge passageway 20 such that vacuum gauge 22 may be attached and connected to the chamber via passageway 20. Wall 12 also defines a inlet passageway 24 at the first end 14 of said wall 12 and an outlet passageway 26 at said second end 16 of said wall 12. Outlet passageway 26 is connected via conduit 28 to vacuum pump 30. Vacuum pump 30 is connected to vacuum outlet conduit 32. Vacuum conduit 32 has a tee branch conduit 34 extending therefrom and having a valve 36 attached to it. Valve 36 when open allows communication to the atmosphere. The second end of conduit 32 is attached to recycle valve 38, and the other side of recycle valve 38 is attached to conduit 40, which is connected to passageway 24 of wall 2. If desired, the outlet conduit may have a purge conduit 35 communicating with it and a purge valve 37 which may be opened or closed as desired to allow atmospheric gases to reenter the chamber upon completion of the development of prints opened at the end of the cycle. Valve 37 is, when incorporated into the device, in the closed position to evacuate the chamber and opened at the end of the cycle.

Removable end cap 42 is dimensioned to close off the first end 14 of said chamber 13 in such a manner to form a substantially air tight seal. End cap 42 is preferably provided with seal 44. In the preferred embodiment end cap 42 has a projecting rim 46, which will slide over wall 12. Also in the preferred embodiment, seal 44 is recessed within channel 48 and the interior surface of end cap 42 has a diameter D slightly smaller than the inside diameter of wall 12. This design of the end cap 42 is preferred, because in operation when the removable end cap 42 is placed over the opening at the first end 14 of the chamber and the chamber evacuated, the removable end cap 42 will be sucked firmly against first end 14 of wall 12. This will cause seal 44 to press against end wall 14, forming a tight seal. The inner face with diameter D and the channel 48 construction helps prevent the seal 44 from being sucked into the chamber 13 as vacuum is created in the chamber.

In operation the item on which fingerprints are to be developed is placed within the chamber. A small amount of cyanoacrylate ester is placed in the chamber in an open cup. Removable end 42 is placed over first end 14 of the chamber. Valve 38 is closed such that air will not pass through recycle conduit 40. Valve 36 is opened such that conduit 32 communicates with the atmosphere. Pump 30 is started and draws air from the chamber 13. When the vacuum gauge 22 indicates the desired vacuum pressure, usually in the range of about 20 to about 25 inches of mercury, valve 36 is closed and valve 38 is open, thereby recycling the remaining gases in the evacuated chamber from the first end of chamber 14 through to the second end 16 of the chamber. Preferably the chamber is evacuated to a pressure in the range of from about 20 to about 25 inches of mercury.

As the pressure in the chamber is reduced, the cyanoacrylate ester boils, releasing fumes. In general, because of the reduced pressure, it is not necessary to heat the cyanoacrylate ester in order for it to boil. If the chamber is in a room which is substantially below room temperature (72° F.), the cyanoacrylate ester may need to be heated for best performance. These fumes produced by boiling the cyanoacrylate ester are then recycled at the desired pressure and react with moisture left in latent prints, forming an accurate representation of the latent fingerprint. The remaining gas and ester fumes are recycled through the chamber for a predetermined period of time sufficient to develop the prints, which will depend somewhat on the volume of the chamber. Generally about 25 to 35 minutes is sufficient for a chamber with an inside diameter of about 15 inches and a length of about 52 inches.

Figure 5:
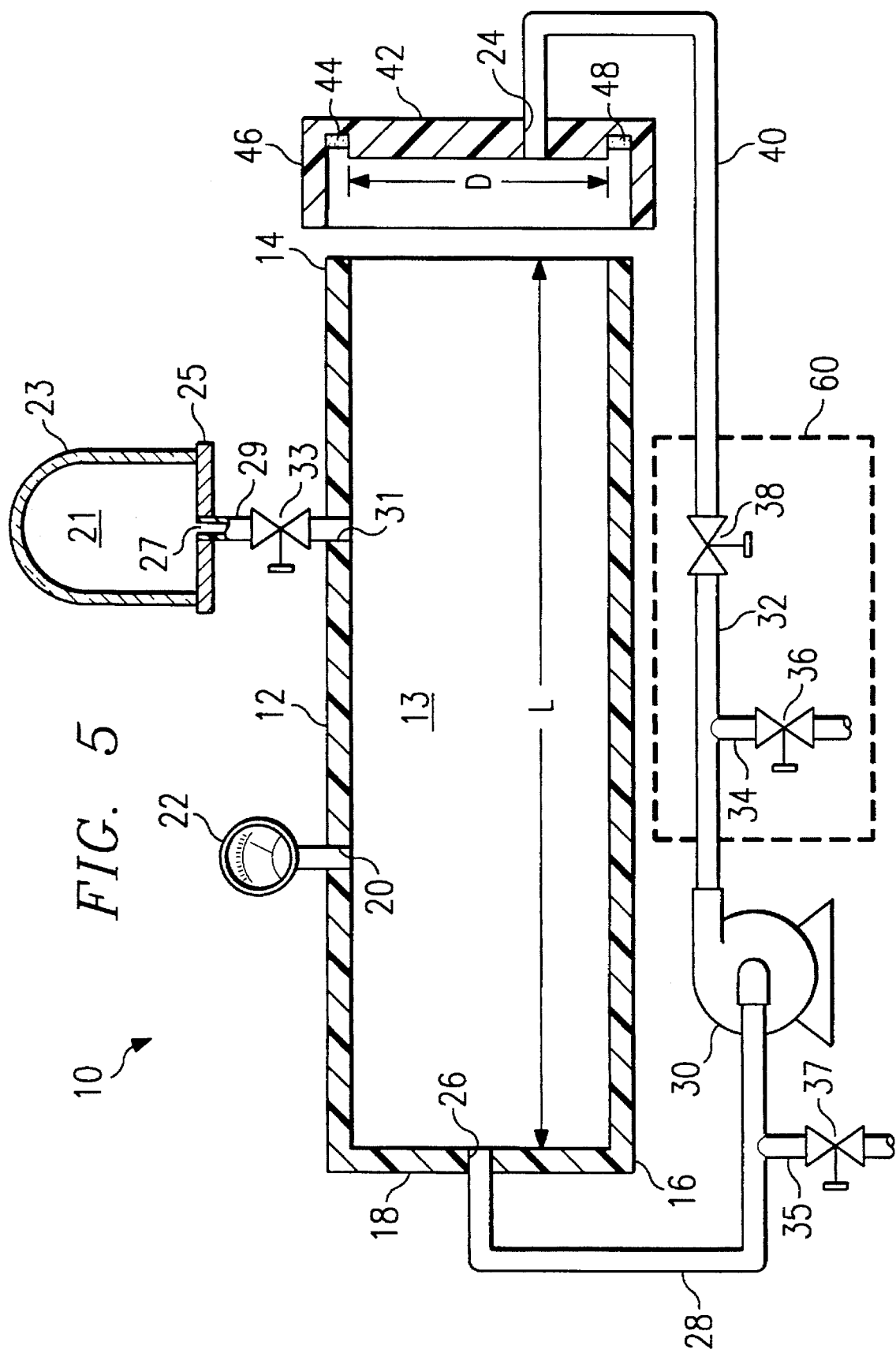
FIG. 5 is a cross sectional view of an alternative embodiment of the present invention.

An important feature of the present invention is a design to obtain good flow of the ester throughout the entire length of the chamber and to prevent localized dead spots or eddies in the chamber where circulation of the ester fumes is not good. Therefore, in the preferred embodiment as shown in figure wall 12, the wall has a length L, and the inlet passageway 24 is X distance from the first end 14, and the outlet passageway 26 is Y distance from the second end 16. Preferably, the inlet passageway 24 and outlet passageway 26 are spaced apart about ½ L or more. Thus X in the preferred embodiment is about ¼ L or less, and Y is about ¼ L or less. If desired, the inlet and outlet passageways (as shown in FIG. 5) can also be located in the ends of the chamber rather than the wall (as shown in FIG. 5). The placement of vacuum gauge passageway 20 can vary greatly. In the preferred embodiment the vacuum passageway is located at between ¼ L and ¾ L from the front end. In the most preferred embodiment the vacuum passageway is about midway between the inlet and outlet passageway.

More preferably the inlet and outlet conduits are within ⅛ of L from the first and second ends respectively. It will be appreciated by those skilled in the art that positioning of the inlet conduit at either the first end or the second end is a matter of choice.

The apparatus can include an optional additional chamber 21 defined by bell jar 23 and bell jar support plate 25. Bell jar 23 is removable from bell jar support plate 25 which defines a passage 27 connected to the first end of conduit 29 which is connected to passageway 31 in wall 12. Thus chambers 21 and 13 are connected. Valve 33 can optionally be provided to close chamber 21. The bell jar allows for small items to be processed. Preferably the jar is transparent so that the sample may be observed during development.

Figure 2:
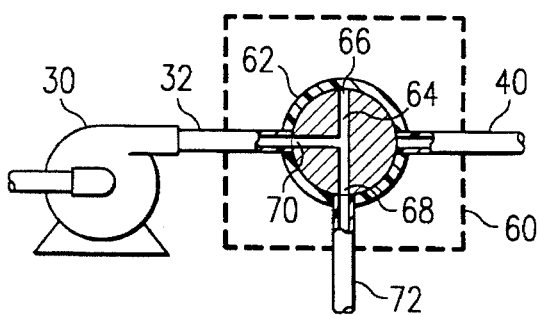
FIG. 2 is a cross sectional view of an alternate valve assembly useful in the present invention.

The valve assembly may be of different configurations. The valve assembly in FIG. 1 is indicated by dashed box 60. In FIG. 1 the valve assembly includes two separate values. FIG. 2 shows an alternate valve assembly contained within dashed box 60. Valve 62 is has a tee-shaped passageway 64 having three openings 66, 68 and 70. The valve is shown positioned in the exhaust position such that conduit 32 communicates with opening 70 and outlet conduit 72 communicates with valve opening 68. Thus, in this configuration the vacuum pump exhausts air to the atmosphere. When the desire vacuum is obtained in the chamber, the valve is rotated such that valve passageway opening 68 communicates with conduit 32 and valve opening 66 communicates with conduit 40 as shown in FIG. 2A. Valve opening 70 is sealed against the valve body. In this way the remaining gas in the chamber is recycled by the vacuum pump. In this construction one valve replaces the two valves shown in FIG. 1. The embodiment shown in FIGS. 2 and 2A has the benefit that one cannot inadvertently continue to exhaust gas when it was desired to recycle the gas. The valve has appropriate stops in it to prevent rotation into a position which would allow simultaneous exhaust and recycle of gas.

Figure 2B:
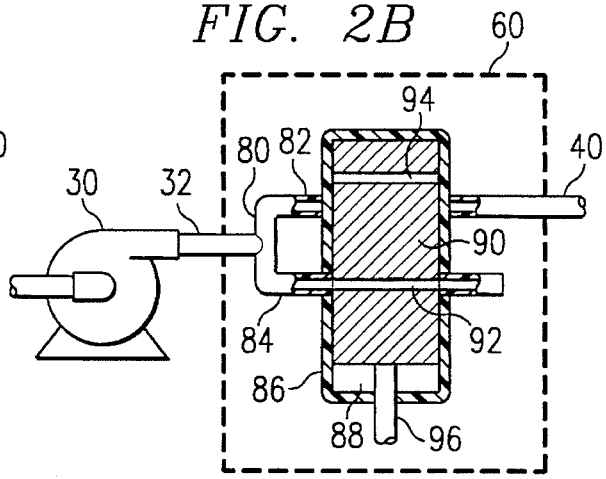
FIG. 2B is a cross sectional view of an alternate valve assembly useful in the present invention.
Figure 2A:
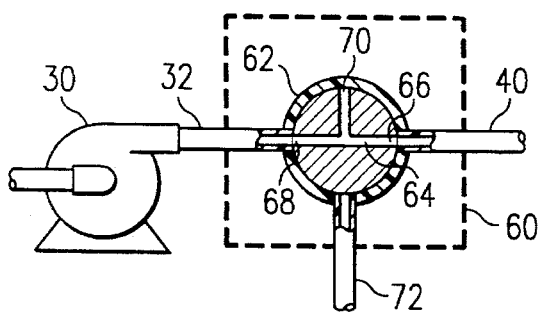
FIG. 2A is a cross sectional view of an alternate valve assembly useful in the present invention.

FIG. 2B shows another embodiment of the valve assembly 60. In this assembly conduit 32 leads into a manifold 80 having a recycle branch 82 and a vent branch 84 connected to valve body 86. Valve body 86 defines a passageway 88 through which valve core 90 travels. Valve core 90 defines two passageways, exhaust passageway 92 and recycle passageway 94. The vent and recycle passageways 92 and 94 of valve core 90 are spaced apart and dimensioned such that recycle branch 82 and recycle passageway 94 will communicate when the valve core is in a second first position, and not be aligned. Vent branch 84 and vent passageway 92 will align (shown in FIG. 2B). In the second position recycle passageway 94 does not align with manifold recycle branch 82, and thus there is no recycle of gases to the chamber. In operation the valve case 990 is set to the first position, the vacuum pump is started and the air within the chamber is evacuated to the atmosphere. When the desired pressure is reached, the valve core 90 is moved to the second position and the remaining gases are recycled through the chamber.

Figure 3:
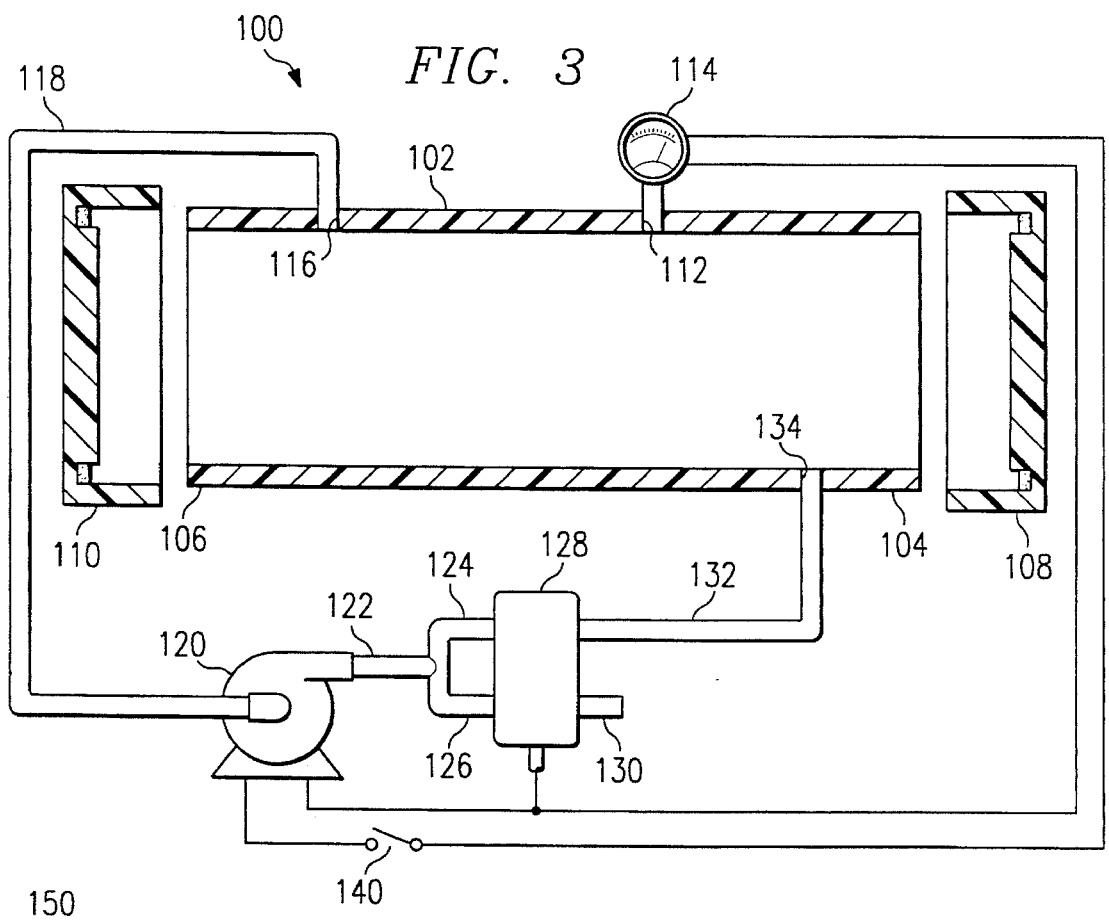
FIG. 3 is a cross sectional view of an alternative embodiment of the present invention.

FIG. 3 shows an automated version of the present invention. Shown generally by 100 is vacuum chamber formed by wall 102 defining an open volume. In the illustrated embodiment the wall 102 is cylindrical. Wall 102 is open at the first end 104 and at second end 106. Two removable end caps 108 and 110 are provided. Preferably they are constructed as described for the end cap in FIG. 1. A vacuum chamber is formed by placing first and second end caps 108 and 110 on to first and second ends of wall 102. The chamber thus formed has and defines at least three openings. In the illustration the openings are shown to be in wall 102. However, it is to be understood that one or more openings could be provided in the end walls but that such positioning is less desirable. Vacuum gauge passageway 112 is connected to gauge switch 114 device, which is a pressure activated switch such that when the pressure in the chamber reaches a desired level, the switch will be engaged. As illustrated, connected to passageway 112 is vacuum gauge switch 114. If desired, the vacuum gauge switch can also provide a visual readout. Outlet passageway 116 communicates with outlet conduit 108 having first and second ends, the first end attached to outlet passageway 116 and the second end at conduit 118 attached to vacuum pump 120. Outlet of vacuum pump 120 is connected to conduit 122, which branches into a recycle branch 124 and a vent branch 126. Branches 124 and 126 are connected to valve assembly 128. Connected with valve assembly 128 are vent conduit 130 and recycle conduit 132. Recycle conduit 132 is connected and communicates to the inside of the chamber via passageway 134. Valve assembly 126 can be designed as described in FIG. 2B and actuated by a solenoid.

In operation of the device shown in FIG. 3 items on which latent finger prints are to be developed are placed in the vacuum chamber 100 and the end caps 108 and 110 are placed in position. Cyanoacrylate ester has also been placed in the chamber. After the end caps have been placed in position, switch 140 is closed, thereby energizing vacuum pump 120 and solenoid valve 128 is positioned such that the gas vacuum chamber 100 is vented to the atmosphere and recycle conduit 132 is sealed, preventing recycle. When the desired level of vacuum is reached in the chamber, the vacuum gauge switch 114 is triggered, thereby releasing the solenoid and allowing the valve assembly to move to the recycle position where the vent is sealed off and communication between passageway 124 and 132 is obtained such that the remaining gas in the vacuum chamber is recycled.

Figure 4:
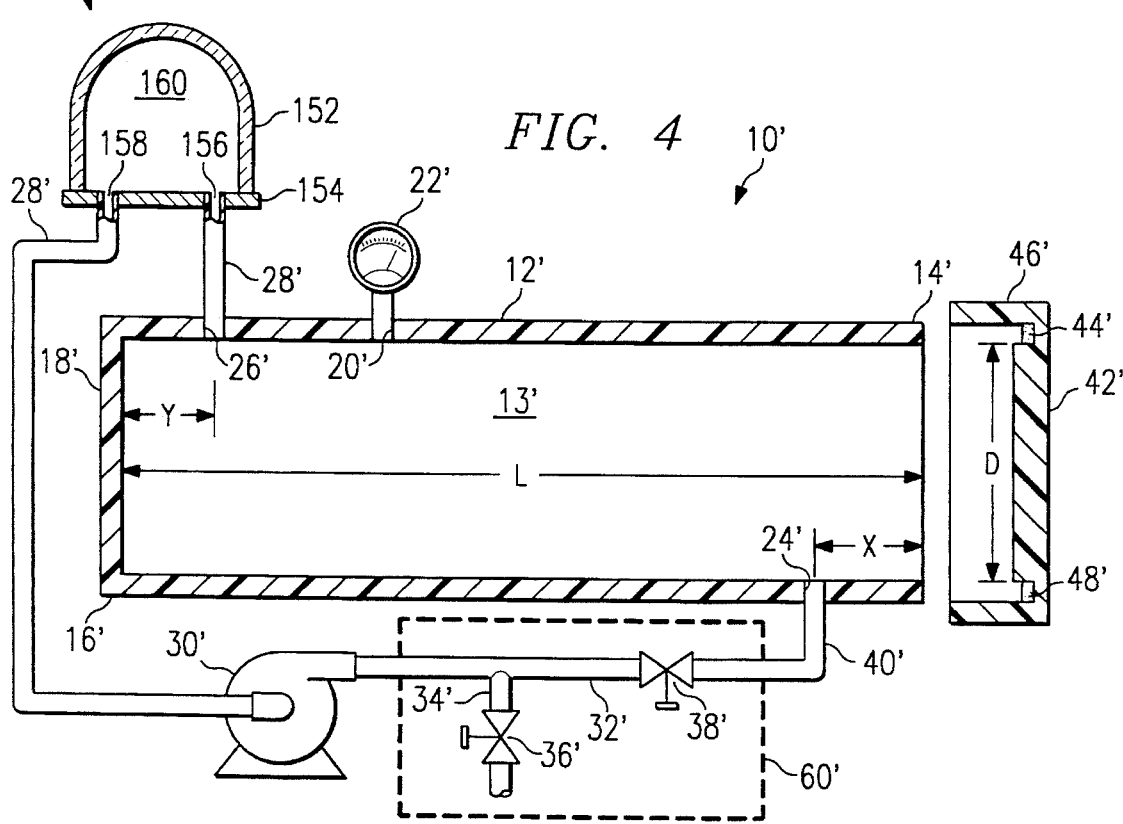
FIG. 4 is a cross sectional view of an alternative embodiment of the present invention.

FIG. 4 shows an alternate embodiment of the present invention. Like components of the apparatus shown in FIG. 4 that are shown in FIG. 1 are indicated by corresponding numbers followed by a ("prime"). The construction and apparatus is the same with the exception that interposed in conduit 28 prime is an auxiliary vacuum chamber generally indicated as 150 composed of a bell jar 152, which is removably supported on bell jar support plate 154. Bell jar support plate 154 defines an inlet passageway 156 and an outlet passageway 158. The outlet conduit 28 from the chamber 13 prime is connected to the inlet passageway 156 of support plate 154, thus communicating with the chamber 160 formed by the bell jar 152 and the support plate 154. Connected to the outlet passageway 158 of the support plate is a second section of conduit 28 prime, which then is connected to the inlet of vacuum pump 30 prime. The auxiliary apparatus 150 may be interposed in inlet vacuum line 40 prime if desired. This particular construction offers the advantage that the atmosphere in chamber 160 is also circulated to give better development of prints and is preferable over the auxiliary chamber 21 shown in FIG. 1. Bell jar 150 is preferably made of glass so that the operator can view development of prints on small objects placed in the bell jar.

It will be appreciated by those skilled in the art that any valve assembly can be used with the automation and that separate valves as shown in FIG. 1 can be employed with separate solenoids actuating the valves.

The present invention is preferably made by any suitable material which will create a substantially airtight chamber. It has been found that a very economical chamber can be made utilizing schedule 40 PVC pipe with a wall thickness of 7/16 inches having an outside diameter from approximately 15.25 inches. Overall length of the chamber can be of any desired length which is sufficient to accept items to be developed. It has been found that a convenient length for a chamber is from about 45 to 55 inches in order to accept rifles. Vacuum lines can be either metal conduit or plastic tubing. A suitable vacuum pump is one sold by Thomas Air Model #2617CE44930, which operates at 115 volts drawing 3.9 amps at 60 Hz. The end caps are also suitably made of ¾-inch PVC and the centers of end caps may be thickened to provide extra rigidity to resist the forces applied to the end cap in the vacuum mode.

It is preferred that the chamber pressure be reduced to no more than about 20 inches of mercury. Below that level of vacuum the moisture contained in the latent fingerprints tends to burn off or boil off and thus destroys the print.

The above description of the preferred embodiments of the invention does not limit the scope of the invention. Various modifications and additions will be obvious to those skilled in the art.

I claim:

1. A vacuum chamber to use in the developing of latent fingerprints comprising:

(a) a wall defining a volume having a first and second end, said wall also defining a vacuum gauge passageway, an inlet passageway, and an outlet passageway;

(b) an end plate connected to the first end of said wall forming a substantially airtight seal;

(c) a removable second end plate for sealing said second end of said wall to form a substantially airtight seal;

(d) an outlet conduit attached to said outlet passageway;

(e) a vacuum pump having an inlet and an outlet, said vacuum pump connected to the outlet conduit;

(f) a vacuum outlet conduit attached to the outlet of said vacuum pump and connected to said inlet passageway and having a valve assembly interposed therein to selectively vent air from the chamber formed by said wall and end pieces to the atmosphere, or to recycle gases remaining in the chamber; and (g) a vacuum gauge attached to said vacuum gauge passageway.

2. The assembly of claim 1 wherein said valve assembly further comprises:

(a) a recycled conduit attached to said inlet passageway;

(b) a first vent valve attached to said vacuum outlet conduit, said valve being connected to a vent conduit to the atmosphere and to said recycle conduit; and (c) a recycle valve interposed in the recycle conduit between said vent valve and said recycle conduit attached to said inlet passageway, said valve having a first position allowing flow through the recycle conduit and a second position which prevents flow through said recycle conduit.

3. The apparatus of claim 1 wherein said valve assembly further comprises:

(a) a recycle branch conduit and a vent branch conduit communicating with said vacuum outlet conduit, a valve body connected to said recycle branch conduit and vent branch conduit;

(b) a valve core positioned within said valve body such that in a first position the vent branch conduit may be aligned with the passageway in said valve core to permit exhaust to the atmosphere; and a second position wherein said vent branch conduit is sealed and said recycle branch conduit is in communication with said recycle conduit to permit recycle of gases in said vacuum chamber while preventing exhaust to the atmosphere.

4. The apparatus of claim 3 wherein said wall has a length L;

said inlet passageway is a distance X from said first end of said wall and;

said outlet passageway is a distance Y from said second end of said wall;

and wherein X and Y are about ¼ L or less.

5. The apparatus of claim 1 further comprising a vacuum switch attached to said vacuum gauge.

6. The apparatus of claim 1 wherein said wall has a length L;

said inlet passageway is a distance X from said first end of said wall and;

said outlet passageway is a distance Y from said second end of said wall;

and wherein X and Y are about ¼ L or less.

7. A vacuum chamber to use in the developing of latent fingerprints comprising:

(a) a wall defining a volume having a first and second end, said wall also defining a vacuum gauge passageway, and an inlet passageway;

(b) an end plate connected to the first end of said wall forming a substantially airtight seal and containing an outlet passageway;

(c) a removable second end plate for sealing said second end of said wall to form a substantially airtight chamber;

(d) an outlet conduit attached to said outlet passageway;

(e) a vacuum pump having an inlet and an outlet, said vacuum pump connected to the outlet conduit;

(f) a vacuum outlet conduit attached to the outlet of said vacuum pump to selectively vent air from the chamber formed by said wall and end pieces to the atmosphere;

(g) a valve mechanism connected to said outlet conduit to selectively vent air from said chamber to the atmosphere or to recycle gases remaining in the chamber by connecting the vacuum outlet conduit to said inlet passageway; and (h) a vacuum gauge attached to said vacuum passageway.

8. The vacuum chamber of claim 7 further comprising a valve assembly connected to said outlet passageway to provide communication of the passageway with the atmosphere.

9. A vacuum chamber to use in the development of latent fingerprints comprising:

(a) a wall defining a volume having a first and second end, said wall also defining a vacuum gauge passageway and inlet passageway and an outlet passageway;

(b) a first removable end plate for sealing the first end of said wall forming a substantially airtight seal;

(c) a second removable end plate for sealing said second end of said wall to form a substantially airtight seal;

(d) an outlet conduit is attached to said outlet passageway;

(e) a vacuum pump having an inlet and outlet, said vacuum pump connected to the outlet conduit;

(f) a vacuum outlet conduit attached to said outlet of said vacuum pump and connected to said inlet passageway;

(g) a valve assembly interposed in said vacuum outlet conduit to selectively vent air to the atmosphere or to recycle gases; and (h) a gauge assembly attached to said vacuum passageway.

10. The apparatus of claim 9 further comprising:

(a) a bell jar support plate having an inlet passageway and an outlet passageway;

(b) said inlet passageway connected to said outlet conduit intermediate the said wall and said vacuum pump and said outlet passageway of said plate connected to said outlet conduit intermediate of said inlet passageway of said vacuum plate and the vacuum pump;

(c) a bell jar removably positioned on said bell jar plate forming a substantially airtight seal.

11. The apparatus of claim 9 further comprising;

(a) a solenoid attached to said valve assembly for opening and closing said valve assembly;

(b) a switch for activating said solenoid to a first position; and (c) a vacuum gauge switch activating said solenoid to a second position.

12. The apparatus of claim 11 wherein said wall has a length L;

said inlet passageway is a distance X from said first end of said wall and;

said outlet passageway is a distance Y from said second end of said wall;

and wherein X and Y are about ¼ L or less.

13. The apparatus of claim 9 wherein said wall has a length L;

said inlet passageway is a distance X from said first end of said wall and;

said outlet passageway is a distance Y from said second end of said wall;

and wherein X and Y are about ¼ L or less.

* * * * *